(12) United States Patent
Mitsuhashi et al.

(10) Patent No.: US 10,542,745 B2
(45) Date of Patent: Jan. 28, 2020

(54) PORTABLE DEVICE FOR EX VIVO STIMULATION OF WHOLE BLOOD

(75) Inventors: Masato Mitsuhashi, Irvine, CA (US); Taku Murakami, Irvine, CA (US)

(73) Assignees: Hitachi Chemical Co., Ltd., Tokyo (JP); Hitachi Chemical Company America, Ltd., San Jose, CA (US)

( * ) Notice: Subject to any disclaimer, the term of this patent is extended or adjusted under 35 U.S.C. 154(b) by 628 days.

(21) Appl. No.: 13/883,269

(22) PCT Filed: Oct. 31, 2011

(86) PCT No.: PCT/US2011/058624
§ 371 (c)(1),
(2), (4) Date: May 2, 2013

(87) PCT Pub. No.: WO2012/061307
PCT Pub. Date: May 10, 2012

(65) Prior Publication Data
US 2013/0226032 A1 Aug. 29, 2013

Related U.S. Application Data

(60) Provisional application No. 61/443,907, filed on Feb. 17, 2011, provisional application No. 61/410,223, filed on Nov. 4, 2010.

(51) Int. Cl.
*A01N 1/02* (2006.01)
*A61B 5/15* (2006.01)

(52) U.S. Cl.
CPC ...... *A01N 1/0284* (2013.01); *A61B 5/150206* (2013.01)

(58) Field of Classification Search
CPC . A61B 10/007; A61B 10/0045; A61B 5/1405; A61B 5/1438; A61B 5/15003; A61B 5/150351
USPC .......................................... 600/573, 576, 577
See application file for complete search history.

(56) References Cited

U.S. PATENT DOCUMENTS

| 4,293,078 | A | 10/1981 | Percarpio |
| 5,354,950 | A * | 10/1994 | Golane ............ B32B 7/02 206/709 |
| 7,026,929 | B1 | 4/2006 | Wallace |
| 2006/0204950 | A1 | 9/2006 | Ilercil et al. |
| 2008/0135564 | A1 * | 6/2008 | Romero ............ B65D 81/3827 220/592.2 |
| 2009/0139261 | A1 | 6/2009 | Nakano et al. |

(Continued)

FOREIGN PATENT DOCUMENTS

| JP | 1996285839 | 1/1996 |
| WO | 20060091934 | 8/2006 |
| WO | 2009073152 | 6/2009 |

OTHER PUBLICATIONS

Extended European Search Report dated Nov. 7, 2013 (EP 11 83 8631) corresponding to PCT/US2011/058624.

(Continued)

*Primary Examiner* — Daniel L Cerioni
(74) *Attorney, Agent, or Firm* — Knobbe Martens Olson & Bear LLP

(57) ABSTRACT

Disclosed are methods, device kits, and systems for improved quantification of mRNA from whole blood. More particularly, the devices and kites related thereto are useful for the controlled and repeatable ex vivo stimulation of whole blood.

19 Claims, 12 Drawing Sheets

Orderform

Shipping address
Shipper's name & address

(56) References Cited

U.S. PATENT DOCUMENTS

2009/0155838 A1    6/2009  Hale
2009/0204190 A1*   8/2009  Sestito ..................... A61F 7/10
                                                            607/108
2010/0047730 A1    2/2010  Fergueson et al.

OTHER PUBLICATIONS

Engel, "Engel 14-digital display EMS Fridge/Freezer/Heater", 2010, published Jul. 19, 2010; <URL: http://web.archive.org/web/20100719005130/http://www.bigfrogmountain.com/Engel%2015%20EMS.html>.

MicroQ Technologies Portable Shipping Incubators, 2013 <URL: http://www.microQ.com/producst.php>; retrieved from the internet Apr. 29, 2013.

Sep. 2, 2014 Office Action in related Japanese Application No. 2013-537749 (PCT/US2011/058624) and English Translation.

* cited by examiner

PORTABLE DEVICE FOR EX VIVO STIMULATION OF WHOLE BLOOD

RELATED APPLICATIONS

The contents of each of the priority applications listed in the accompanying Application Data Sheet is incorporated in its entirety by reference herein.

FIELD OF THE INVENTION

Embodiments of the present invention relate generally to portable devices capable of generating and maintaining controlled environmental conditions within the device. Several embodiments relate generally to the use of the devices for the ex vivo treatment and stimulation of whole blood.

DESCRIPTION OF THE RELATED ART

Research in the field of molecular biology has revealed that the genetic origin and functional activity of a cell can be deduced from the study of its ribonucleic acid (RNA). This information may be of use in clinical practice, to diagnose infections, to detect the presence of cells expressing oncogenes, to detect familial disorders, to monitor the state of host defense mechanisms and to determine the HLA type or other marker of identity. RNA exists in three functionally different forms: ribosomal RNA (rRNA), transfer RNA (tRNA) and messenger RNA (mRNA). Whereas stable rRNA and tRNA are involved in catalytic processes in translation, mRNA molecules carry genetic information. Only about 1-5% of the total RNA consists of mRNA, about 15% of tRNA and about 80% of rRNA.

mRNA is an important diagnostic tool, particularly when it is used to quantitatively observe up- or down-regulation of genes. Human peripheral blood is an excellent clinical resource for mRNA analysis. The detection of specific chimeric mRNA in blood, for example, indicates the presence of abnormal cells and is used in molecular diagnostics for chronic myelogenous leukemia (CML) (Kawasaki E. S., Clark S. S., Coyne M. Y., Smith S. D., Champlin R., Witte O. N., and McCormick F. P. 1988. Diagnosis of chronic myeloid and acute lymphocytic leukemias by detection of leukemia-specific mRNA sequences amplified in vitro. Proc. Natl. Acad. Sci. USA 85:5698-5702, Pachmann K., Zhao S., Schenk T., Kantarjian H., El-Naggar A. K., Siciliano M. J., Guo J. Q., Arlinghaus R. B., and Andreeff M. 2001. Expression of bcr-abl mRNA individual chronic myelogenous leukaemia cells as determined by in situ amplification. Br. J. Haematol. 112:749-59). Micrometastatic cancer cells can also be detected in blood by measuring cancer-specific mRNA, such as carcinoembryonic antigen (CEA) for colon cancer, prostate specific antigen (PSA) for prostate cancer, thyroglobulin for thyroid cancer (Wingo S. T., Ringel M. D., Anderson J. S., Patel A. D., Lukes Y. D., Djuh Y. Y., Solomon B., Nicholson D., Balducci-Silano P. L., Levine M. A., Francis G. L., and Tuttle R. M. 1999. Quantitative reverse transcription-PCR measurement of thyroglobulin mRNA in peripheral blood of healthy subjects. Clin. Chem. 45:785-89), and tyrosinase for melanoma (Pelkey T. J., Frierson H. F. Jr., and Bruns D. E. 1996. Molecular and immunological detection of circulating tumor cells and micrometastasis from solid tumors. Clin. Chem. 42:1369-81). Moreover, as the levels of these cancer-specific mRNA can change following treatment, quantification of specific mRNA provides for a useful indicator during treatment follow-up.

As blood contains large quantities of non-nucleated erythrocytes (approximately 5 million cells/μL) compared to leukocytes (approximately 5000 leukocytes/μL), the isolation of granulocytes or lymphocytes from whole blood is commonly performed as the first step in mRNA analysis. However, due to inconsistencies in the recovery of specific subsets of leukocytes among different samples, the number of isolated leukocytes is determined for each sample and results are often expressed as the quantity of mRNA per leukocytes, not mRNA/μL blood. Moreover, mRNA quantities may change during lengthy isolation processes.

The scientific community is facing a huge problem of institute-to-institute and experiment-to-experiment variation in gene expression analysis, because of the lack of standardization. Although recent gene amplification technologies provide an absolute quantity of template DNA, these values cannot be converted to the amounts of the gene in the original materials, due to the lack of information of the yield of RNA recovery and the efficiency of cDNA synthesis in each sample. Total RNA is frequently used as a standardization marker for mRNA quantitation, and results are typically expressed as the amounts of genes per μg total RNA. However, it must be emphasized that total RNA does not represent mRNA, because the fraction of mRNA is only 1-5% of total RNA, and mRNA volume varies even when the amounts of total RNA is identical. The yield of total RNA or mRNA also varies widely depending on which method is employed. Once RNA is extracted, the next step is the synthesis of cDNA, which itself can create uncertainty since existing methods do not indicate whether each RNA template creates a single copy of cDNA in each experiment. In order to avoid the above problems, relative quantitation is used widely by comparing the data of target genes to that of housekeeping genes or rRNA. However, the amounts of control genes are typically not consistent and may change during experiments. Moreover, this variation presents a serious problem for clinical diagnostics, since each clinical specimen is typically analyzed at a different point in time.

It is typically very difficult to isolate pure mRNA from whole blood because whole blood contains large amounts of RNAases (from granulocytes) and non-nucleated erythrocytes. Although various RNA extraction methods are available for whole blood applications (de Vries T. J., Fourkour A., Punt C. J., Ruiter D. J., and van Muijen G. N. 2000. Analysis of melanoma cells in peripheral blood by reverse transcription-polymerase chain reaction for tyrosinase and MART-1 after mononuclear cell collection with cell preparation tubes: a comparison with the whole blood guanidinium isothiocyanate RNA isolation method. Melanoma Research 10:119-26, Johansson M., Pisa E. K., Tormanen V., Arstrand K., and Kagedal Bl. 2000. Quantitative analysis of tyrosinase transcripts in blood. Clin. Chem. 46:921-27, Wingo S. T., Ringel M. D., Anderson J. S., Patel A. D., Lukes Y. D., Djuh Y. Y., Solomon B., Nicholson D., Balducci-Silano P. L., Levine M. A., Francis G. L., and Tuttle R. M. 1999. Quantitative reverse transcription-PCR measurement of thyroglobulin mRNA in peripheral blood of healthy subjects. Clin. Chem. 45:785-89), the assay procedures are labor-intensive, require several rounds of centrifugation, and involve careful handling that is essential in eliminating ribonuclease activities.

SUMMARY

In several embodiments, there is provided herein a system for the ex vivo stimulation of blood during transport of the blood comprising a portable device capable of generating and maintaining at least two temperature ranges within the device, the device comprising an insulated device shell having an internal cavity, a heating source, and a cooling source. In several embodiments the internal cavity is dimensioned to contain a one or more blood collection tubes. In several embodiments the heating source is capable of maintaining the temperature within the device at a first temperature in a range between about 25° C. and 40° C. for at least one hour after activation of the heating source and maintain the temperature around the maintained temperature within ±2.5° C. In several embodiments, the cooling source is capable of maintaining the temperature within the device at a second temperature range below room temperature for at least 4 hours with a temperature fluctuation around the maintained temperature being within ±5° C.

In one embodiment, the first temperature phase comprises a maintained temperature of 37° C.±2.5° C. In one embodiment the second temperature phase comprises a maintained temperature of 4° C.±5° C.

In several embodiments, the system further comprises a plurality of blood collection tubes, the blood collection tubes comprising an anti-coagulant and a stimulating agent. In several such embodiments, the stimulant comprises one or more of a chemotherapeutic drug, immunomodulatory agent, vaccine, adjuvant, recombinant protein, monoclonal antibody, lectin, derivatives from infectious agents, allergens, and combinations thereof. In several embodiments, the system further comprises a second plurality of blood collection tubes comprising an anti-coagulant and a corresponding control solvent of the stimulating agent.

In several embodiments, the blood collection tubes comprise a non-glass tube having a pressure within the collection tube that is negative as compared to the pressure outside of the collection tube, one or more anticoagulants, one or more leukocyte stimulating agents; and a puncturable self-sealing cap that seals the collection tube. In some embodiments, the blood collection tubes further comprise a visible marker of that is activated by negative pressure.

In several embodiments, the system further comprises a temperature recording device, wherein the device serially records the temperature within the cavity for later retrieval.

In several embodiments, the system further comprises at least one additional insulating container configured to be placed within the portable device and to contain the heating device and the blood collection tubes.

In some embodiments, the heating source is battery operated. In some embodiments, the heating source is operated by one or more primary (disposable) batteries. In some embodiments, the heating source is operated by one or more secondary (rechargeable) batteries. In other embodiments, the heating source generates heat through a chemical reaction.

In several embodiments the temperature recording device is battery operated. In some embodiments, the temperature recording device is operated by one or more primary (single-use) batteries. In some embodiments, the temperature recording device is operated by one ore more secondary (rechargeable) batteries. In some embodiments, the cooling source comprises a re-usable coolant.

In several embodiments, there is provided a non-glass blood collection tube for the collection of blood by negative pressure comprising a non-glass tube, one or more anticoagulants, one or more leukocyte stimulating agents, a visible marker of that is activated by negative pressure, and a puncturable self-sealing cap that seals the collection tube. In several embodiments, the pressure within the collection tube is negative as compared to the pressure outside of the collection tube, thereby allowing precise volumes of blood to be collected, based on the negative pressure within the tube.

In several embodiments, the one or more leukocyte stimulating agents are selected from the group consisting of: chemotherapeutic drugs, immunomodulatory agents, vaccines, adjuvants, recombinant proteins, monoclonal antibodies, lectins, derivatives from infectious agents, allergens, and combinations thereof.

In some embodiments, the one or more anticoagulants comprises heparin. In other embodiments, other anticoagulants are used in addition to or in place of heparin.

In several embodiments, the tube is suitable for incubation at a temperature between about 25° C. and 40° C. for at least about one hour. Moreover, in several embodiments, the tube is suitable for storage at temperatures sufficiently low to freeze a blood sample, and wherein the collection tube is structurally stable at the temperatures (e.g., will not crack or break during freezing/thawing).

In several embodiments, there is also provided a method of obtaining a blood sample comprising, inspecting a non-glass blood collection tube comprising one or more anticoagulants, one or more leukocyte stimulating agents, a visible marker of that is activated by negative pressure, and a puncturable self-sealing cap that seals the collection tube for the presence of an activated visible marker of negative pressure, puncturing a vein of the venous system of the subject if the activated marker is present, puncturing the self-sealing cap, and allowing blood to fill the collection tube until the negative pressure is equalized or until a desired volume is collected.

In several embodiments there is provided a method for ex vivo stimulation of a blood sample, comprising obtaining a blood sample from a subject as described above, placing the blood collection tube comprising the blood sample into a portable device capable of generating and maintaining a controlled environment within the device, wherein the portable device comprises an insulated device shell having an internal cavity dimensioned to contain the blood collection tube, a battery-operated heating source, a cooling source, and activating the battery-operated heating source.

In some embodiments, the heating source is capable of maintaining the temperature within the internal cavity between about 25° C. and 40° C. for at least one hour after activation of the heating source. In some embodiments, the cooling source comprises re-usable coolant and is capable of maintaining the temperature within the device below room temperature for at least 4 hours In some embodiments, the method further comprises inspecting a second non-glass blood collection tube comprising one or more anticoagulants and a control solvent of the one or more leukocyte stimulating agents for the presence of an activated marker of negative pressure, puncturing the self-sealing cap of the non-glass blood collection tube and collecting a second blood sample from the punctured vein of the subject if the activated marker is present, and placing the second blood collection tube comprising the second blood sample into the portable device.

In several embodiments, the method additionally comprises ex vivo analysis of the blood samples, which comprises removing the first and the second blood samples from the portable device and measuring one or more target mRNA or one or more target proteins from the first and the second blood samples.

Additionally, there is provided a method for the ex vivo stimulation of a blood sample comprising collecting a first blood sample from a subject into a blood collection tube comprising a non-glass tube, one or more anticoagulants, and one or more leukocyte stimulating agents, placing the blood collection tube into a system for the ex vivo stimulation of blood as described above and activating the battery-operated heating source, thereby stimulating the blood sample ex vivo.

There is also provided a kit for the ex vivo stimulation of a blood sample, comprising a non-glass blood collection tube for the collection of blood by negative pressure comprising a non-glass tube (wherein the pressure within the collection tube is negative as compared to the pressure outside of the collection tube), one or more anticoagulants, one or more leukocyte stimulating agents, and a puncturable self-sealing cap that seals the collection tube, a portable device capable of generating and maintaining at least two temperature phases within the device, the device comprising an insulated device shell having an internal cavity dimensioned to contain a plurality of the blood collection tubes, a heating source capable of maintaining a temperature within the device between about 25° C. and 40° C. for at least one hour after activation of the heating source and wherein the fluctuation around the maintained temperature is within ±2.5° C.; and a cooling source capable of maintaining the temperature within the device at a second temperature that is below room temperature for at least 4 hours with a temperature fluctuation around the second temperature of within ±5° C.

In several embodiments, the device in the kit maintains the first temperature phase at a maintained temperature of about 37° C.±2.5° C. In several embodiments, the device in the kit maintains the second temperature phase at a maintained temperature of about 4° C.±5° C.

In several embodiments, the kit comprises one or more leukocyte stimulating agents that are selected from the group consisting of: chemotherapeutic drugs, immunomodulatory agents, vaccines, adjuvants, recombinant proteins, monoclonal antibodies, lectins, derivatives from infectious agents, allergens, and combinations thereof.

In several embodiments, the kit comprises one or more anticoagulants comprising heparin, either alone or in combination with additional anticoagulants.

In several embodiments, the blood-collection tubes of the kit are suitable for incubation at a temperature between about 25° C. and 40° C. for at least about one hour. In several embodiments, the blood-collection tubes are suitable for storage at temperatures sufficiently low to freeze a blood sample, and wherein the collection tube is structurally stable at the temperatures.

In several embodiments, there is provided a system for the ex vivo stimulation of blood during transport of the blood, the system comprising a portable device capable of generating and maintaining a controlled environment within the device, the device comprising an insulated device shell having an internal cavity dimensioned to contain a plurality of blood collection tubes, a plurality of blood collection tubes, comprising an anti-coagulant and a stimulating agent, a battery-operated heating source, and a cooling source. In some embodiments, the heating source is capable of maintaining the temperature within the device between about 25° C. and 40° C. for at least one hour after activation of the heating source. In several embodiments, the cooling source comprises re-usable coolant. In some embodiments, the cooling source is capable of maintaining the temperature within the device below room temperature for at least 4 hours. In some embodiments, the cooling source is capable of maintaining the temperature within the device below room temperature for between about 4 and 24 hours. In some embodiments, the system also comprises a second plurality of blood collection tubes comprising an anti-coagulant and a corresponding control solvent of the stimulating agent. In several embodiments, the system further comprises a temperature recording device, wherein the device serially records the temperature within the cavity for later retrieval.

DETAILED DESCRIPTION

Figure 1:
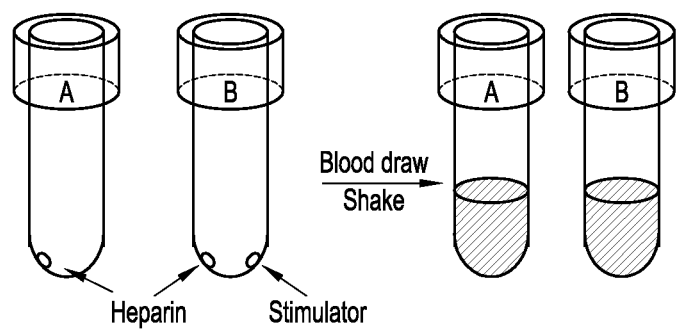
FIG. 1 shows a set of vacuum blood collection tubes filled with blood samples in accordance with some embodiments.

There exists a need for improved methods for ex vivo blood stimulation as well as devices to accomplish such methods. Several existing methods for ex vivo stimulation are dependent on post-blood draw conditions. However, storage of blood for long periods is not physiological and can adversely affect the blood samples and testing. In addition mRNA induction may be altered during storage. Ideally, blood should be stimulated immediately after blood draw. Manipulation of blood, incubation at 37° C., and leukocyte isolation or storage of post-stimulated blood at temperature of −80° C. is not practical in many situations or locations. For example, if blood is drawn at locations outside of sophisticated labs or hospitals then incubation under physiological conditions or storage of post-stimulated blood at a temperature of −80° C. may not be practical.

In addition, a need exists for a portable device capable of being used for the consistent and repeatable ex vivo stimulation of whole blood. A need also exists for a portable device capable of incubating stimulated blood cells and methods of using the same. A need also exists for a portable device capable of isolating and storing leukocytes from post-stimulated blood cells and methods of using the same.

In some embodiments methods and devices are disclosed herein for ex vivo stimulation of whole blood. In several embodiments, the devices disclosed herein are portable. In some embodiments the devices can be used in the field, for example, places outside of hospitals or laboratories. In some embodiments, the devices are configured to be self-regulating, for example, maintain a certain desirable temperature within the device for a certain period of time. In some embodiments, more than one temperature is maintained over time (e.g., sequentially desired temperatures are achieved). In several embodiments, the devices are suitable for sequential use in the stimulation of, incubation and storage of, and transport of whole blood samples, as described in more detail below.

In some embodiments whole blood is collected from a subject into blood vacuum collection tubes. With the relatively straightforward identification and production of gene-specific primers and probes, gene amplification technologies enable the identification and quantification of specific mRNA levels, even from a pool of different genes, making whole blood an ideal material for mRNA analysis. In several embodiments, one or more collection tubes contain a blood stimulating agent. In several embodiments, the collected whole blood is heparinized upon collection. In several embodiments, the whole blood is collected into two or more collection tubes. The stimulating agent can be a liquid or solid. The tubes can be shaken or moved in a manner sufficient to agitate the whole blood and facilitate mixing with the heparin and/or stimulant.

In some embodiments the stimulant comprises a chemotherapeutic drug, immunomodulatory agent, vaccine, adjuvant, recombinant protein, monoclonal antibody, lectin, or derivative from an infectious agent. In some embodiments the chemotherapeutic drug comprises cytarabine, daunorubicin, doxorubicin, idarubicine, etopiside, aclarubicine, or mitoxanthrone. In some embodiments the recombinant protein comprises an interleukin (e.g., interleukin-2 or interleukin-10 and interferons (e.g., interferon gamma). In some embodiments the derivative from infectious agent comprises a purified protein derivative, (e.g., a PPD, such as a tuberculin PPD). Other stimulatory agents such as phytohemaglutinin (PHA), zymosan, tumor necrosis factor, and the like are used.

In some embodiments after the blood is collected into the tubes the blood is incubated under conditions to promote stimulation of the whole blood. In preferred embodiments the blood is incubated under physiological conditions. In some embodiments a temperature of about 37° C. is used to simulate physiological conditions. In some embodiments, temperatures of between about 30° C. and about 33° C., between about 33° C. and about 35° C., between about 35° C. and 37° C., or between about 37° C. and about 39° C. are used. In some embodiments the samples are maintained at physiological temperatures and are incubated for about 30 minutes to about four hours including about 30 minutes to about 1 hour, about 1 hour to about 2 hours, about 2 hours to about 3 hours, about 3 hours to about 4 hours, and overlapping ranges thereof. In some embodiments the incubation can be longer than four hours (e.g., from 4 to 6 hours, from 6 to 8 hours, from 8 to 10 hours, from 10-12 hours, from 12-24 hours, and overlapping ranges thereof).

In some embodiments the samples are placed in a storage container or incubator having a heat source that is capable of heating one or more tubes. Preferably, the heat source in the storage container or incubator is capable of maintaining physiological conditions (e.g., approximately physiological temperature) in the blood samples. In some embodiments the heat source is capable of maintaining physiological conditions in the blood tubes for about 30 minutes to about 4 hours, including about 30 minutes to 1 hour, about 1 hour to about 2 hours, about 2 hours to about 3 hours, about 3 hours to about 4 hours, and overlapping ranges thereof. In several embodiments, incubation times are greater than 4 hours (e.g., about 6-8 hours or 8 hours to overnight). In some embodiments the heat source comprises a heating pad. In some embodiments the heating pad (or other heating device) can be operated with batteries to provide heat. In some embodiments, a timer regulates the operational time of the heater, such that after a desired incubation period, the heater is shut off. In some embodiments, peltier heat sources are used. In some embodiments, self-contained combustible fuel devices are used to generate heat. In some embodiments the heating device can provide heat through an exothermic chemical reaction or process (e.g., a "smack-pack"). In several embodiments, a water jacket is used, wherein water of a desired temperature is circulated through the wall of the incubator in order to heat (or cool) the interior of the incubator to a desired incubation or storage temperature. In several embodiments, an insulator (internal to the device as a whole) is used to place the tubes in close proximity to the heat source to improve the stability of the incubation temperatures over time. Similar to the heating source, in some embodiments, the cooling source may be battery operated or be based on chemical reactions (e.g., urea, ammonium sulfate and water). The cooling system can optionally comprise a generator-like device, such as a Stirling Cooler (FPSC) or an electrical device, such as a Peltier cooler. In some embodiments, self-contained re-usable ice packs are used. In several embodiments, the cooling system maintains the temperature within the device for at least 24 hours (e.g., throughout the transportation of the portable device). In several embodiments, the cooling system is capable of maintaining the temperature within the device for between about 24 to about 72 hours. In some embodiments, this time period includes the incubation period when the heating source is active. As such, in several embodiments, the collection tubes are incubated at physiological temperature while the heating source is active, then, when the heating source is shut off, the collection tubes are stored at a cooler temperature (e.g., to stabilize mRNA) throughout the transport process.

In some embodiments, the storage container or incubator is configured to be transported or shipped to a hospital or lab while maintaining physiological conditions in the blood sample tubes (e.g., shipping the device is concurrent with the stimulation and subsequent cooling of the blood samples). In some embodiments, the blood samples are removed from the storage container or incubator and cooled to a temperature of about −80° C. and stored until later processing and testing. In several embodiments the incubator doubles as the storage container and the user alters the configuration of the incubator (e.g., removes the heating pad and installs an ice pack)

in order to convert the incubator to a storage container. In several embodiments, however, a separate incubator and storage container are used.

In still additional embodiments, a single device functions as an incubator, storage container, and shipping container. For example, in some embodiments, a single insulated device (e.g., container) is provided that comprises a heating source and a cooling source. In some embodiments, the device further comprises a temperature recording device that allows the temperature history within the device to be analyzed. In some embodiments, the device is optionally provided with tubes for collection of blood. In such embodiments, the tubes optionally contain desired stimulating agents, such as those described herein. Thus, a single device is provided that allows for stimulation (e.g., incubation) of blood samples with a stimulating agent for a desired period of time at a physiologic temperature followed by incubation of the stimulated blood samples at a cooler temperature (e.g., at or less than room temperature) for a period of time, each of the above occurring during the shipment of the device to a site for gene expression analysis. Stability of mRNA after stimulation at such temperatures has been established. Despite the stability of the mRNA, the temperature recording device provides a degree of quality control in that samples that were not exposed to proper stimulation conditions (e.g., too low or high a temperature, shortened or extended incubation times, etc.) can be identified and discarded.

Such devices are particularly advantageous for use by blood draw laboratories. In order to avoid the laboratory to laboratory variation in performing ex vivo stimulation, devices such as those disclosed herein are provided to enable controlled and repeatable ex vivo stimulation across multiple laboratories. A laboratory would first obtain blood samples from a patient. In some embodiments, blood is drawn into standard blood collection tubes, but in preferred embodiments, blood is drawn directly into tubes supplied to the laboratory, the tubes containing a desired stimulating agent (or control solvent). In some embodiments, blood draws are optionally performed based on vacuum pressure within the tube, thereby reducing variation due to volume collected. After collection into the stimulant-containing tubes, the tubes are placed into the device, and a heat source and a cooling source are activated. In some embodiments, the heat source and cooling source are integrated into the device, while in some embodiments, a user places the activated sources into the device. In some embodiments, a temperature recording device is optionally activated and placed into the device, while in other embodiments, a temperature recording device is integrated into the device. Finally, the laboratory can seal the device and ship it to a central location for subsequent gene expression analysis. In such embodiments, standard rubber tube caps are used. In other embodiments wherein stimulation and isolation are to take place at the laboratory, described in more detail below, specialized caps comprising an isolation matrix are used.

Figure 6:
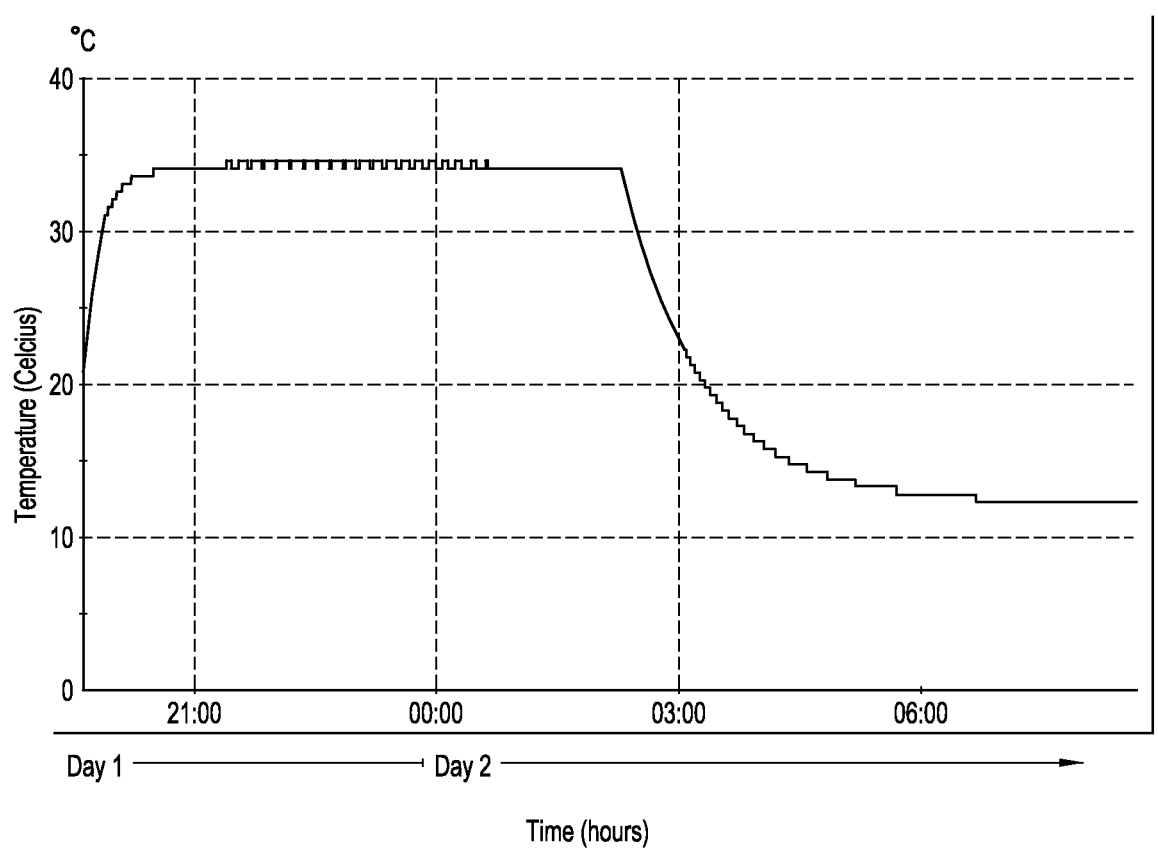
FIG. 6 is graph of temperature over time recorded from the interior of a device in accordance with embodiments described herein.

As described herein, the device is constructed of materials that impart an insulating effect on the environment within the device (e.g. polystyrene foam, fiberglass, etc.). Thus, in combination with the heating source and the cooling source, the device functions to maintain the temperature within the device (e.g., where the blood-containing tubes are placed) at a desired temperature for a desired length of time. In some embodiments, the temperature profile that is maintained begins with an initial period at an approximate physiological temperature (e.g., for stimulation of the blood samples) followed by a secondary period of cooler temperatures (e.g., for stabilization of mRNA post-stimulation). See, for example, FIG. 6. It shall be appreciated that, after stimulation and any associated induction of mRNA, a reduced temperature (vis-à-vis the physiological temperatures imparted by the heating source) is sufficient to maintain the induced mRNA for an extended period of time (sufficient to ship the device to a central lab that can store the samples long-term).

In alternative embodiments, leukocytes may be isolated on site after on site stimulation of the blood samples. After incubation, the tubes containing the blood samples can be removed from the incubator. The caps from the blood tubes can be removed and replaced with caps containing a leukocyte capture membrane. Several leukocyte filter membranes can be layered together to increase the yield of captured leukocytes. In some embodiments the leukocyte capture membrane is positioned on the cap such that when the cap is engaged with the sample tube, the leukocyte membrane faces (e.g., is juxtaposed with) the blood sample. In some embodiments, the cap containing a leukocyte capture membrane also contains moisture adsorbing material and a lid capable of opening to remove the adsorbing material. In some embodiments the leukocyte membrane is at a proximal end of the cap and the water adsorbing material is at the distal end of the cap. In some embodiments the leukocyte capture membrane comprises leukosorb, or other similar fiber or glass matrix suitable for capture of leukocytes.

In some embodiments, the leukocytes can be captured by inverting the sample tube and allowing gravity to pull the sample material through the membrane. In other embodiments, centrifugation, vacuum pressure, positive air pressure, or other similar active means is used to move the sample material through the membrane. The water adsorbing material will adsorb water and other materials, e.g. erythrocytes, from the blood sample, while leukocytes are captured and retained on the filter membrane within the cap.

In some embodiments, the storage container or incubator can be used to store, transport, and/or ship the samples after leukocyte isolation. As discussed above, in some embodiments, the storage container or incubator can cool or heat the samples to maintain desired conditions during shipment and storage. In some embodiments, ambient conditions are used in the storage container. In several embodiments, a second "smack pack" or other cooling or heat production mechanism is used to create a desirable storage temperature (e.g., a multi-temperature profile).

In some embodiments, an mRNA assay is prepared after the leukocytes have been isolated from the blood sample. The mRNA assay can be prepared by subjecting the leukocytes to cell lysis to produce a lysate containing mRNA, transferring the lysate to a GENEPLATE to capture the mRNA, and quantifying the mRNA. In several embodiments, isolation is performed in the field, then frozen for analysis. In some embodiments, conversion of mRNA to cDNA is performed in the field (e.g., outside a laboratory) and then frozen for later amplification analysis (or other variety of gene expression analysis).

In several embodiments using tubes with leukocyte capturing caps, the cap containing the leukocyte capture membrane is removed from the blood collection tube. In some embodiments, the lid on the cap can then be opened to remove the moisture adsorbing material, which may be discarded (or recycled and/or used for additional analysis). A new tube can then be attached to the cap containing the leukocyte capture membrane and leukocytes. A lysis buffer can be added to the tube through the lid used to remove the moisture adsorbing material. The leukocytes that are trapped on the filter membrane are lysed using a lysis buffer to release mRNA from the leukocytes. The transfer of lysate to the geneplate or an additional collection tube may be accomplished using centrifugation, vacuum aspiration, positive pressure, or washing with ethanol followed by vacuum aspiration. The mRNA is quantified by producing cDNA and amplifying the cDNA by PCR. Particularly preferred embodiments use TaqMan PCR to quantify mRNA.

Further detail regarding the composition of lysis buffers that may be used in several embodiments can be found in U.S. patent application Ser. No. 11/376,018, filed Mar. 15, 2006, which is currently pending and which is incorporated in its entirety by reference herein. In several embodiments, cDNA is synthesized from the mRNA. In preferred embodiments, the cDNA is then amplified using real time PCR with primers specifically designed for amplification of certain desired genes (e.g., established or putative disease markers). Further details about the PCR reactions used in some embodiments are also found in U.S. patent application Ser. No. 11/376,018. Further details regarding the quantification of mRNA from whole blood cells can be found in U.S. application Ser. No. 10/796,298 filed Mar. 9, 2004, now issued as U.S. Pat. No. 7,745,180, which is incorporated in its entirety by reference herein.

After the completion of PCR reaction, the mRNA (as represented by the amount of PCR-amplified cDNA detected) for one or more genes (e.g., disease markers) is quantified. In certain embodiments, quantification is calculated by comparing the amount of mRNA encoding one or more markers to a reference value. In other embodiments, the reference value is expression level of a gene that is not induced by the stimulating agent, e.g., a house-keeping gene. House-keeping genes that are well known in the art may also be used as a reference value. In other embodiments, a house keeping gene is used as a correction factor, such that the ultimate comparison is the induced expression level of one or more markers as compared to the same marker from a non-induced (control) sample. In still other embodiments, the reference value is zero, such that the quantification of one or more markers is represented by an absolute number. In several embodiments a ratio comparing the expression of one or more offensive immune markers to one or more defensive immune markers is made. In still other embodiments, no normalization is made.

In certain embodiments a kit is provided comprising a combination of any of the devices disclosed herein. In some embodiments the kit comprises a blood collection vacuum tube with heparin, a blood collection vacuum tube with heparin and a stimulant, and a heating pad (or other heat source) capable of maintaining the blood collection vacuum tubes at a physiological temperature for at least 30 minutes. In some embodiments the kit comprises a storage container capable of storing and shipping one or more blood collection vacuum tubes. In some embodiments the kit comprises a cap comprising a leukocyte membrane and moisture adsorbing material.

EXAMPLES

Specific embodiments will be described with reference to the following examples which should be regarded in an illustrative rather than a restrictive sense.

Example 1—Ex Vivo Blood Stimulation

FIGS. 1-5 show methods and devices for collecting blood, processing the samples, and performing an mRNA assay on the processed blood sample in accordance with some embodiments. As illustrated in FIG. 1, tubes A and B both contain heparin prior to filling with whole blood cells. In other embodiments, heparin (or another anticoagulant) may be added to the tubes manually). Tube A is used as a control because it does not contain any stimulant. Tube B contains a dried stimulant. As above, in some embodiments, a stimulant, including an additional stimulant, is added manually. The blood is collected into the sample tubes followed by shaking or agitating the tubes to ensure that the heparin and/or stimulant mix with the collected blood.

Figure 2:
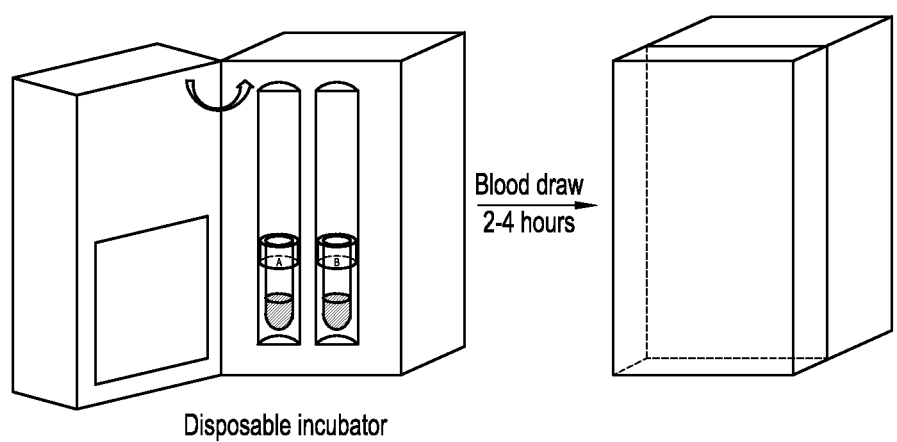
FIG. 2 shows ex vivo stimulation of blood in a storage container or incubator in accordance with some embodiments.

Next, as shown in FIG. 2 a disposable incubator is used to incubate the blood samples of FIG. 1. In several embodiments, incubation is performed under physiological conditions. In some embodiments, a temperature of about 37° C. is used. The disposable incubator has a heating pad capable of heating the samples for 2-4 hours. In other embodiments, time and/or temperature of incubation may be increased or decreased as desired.

Figure 3:
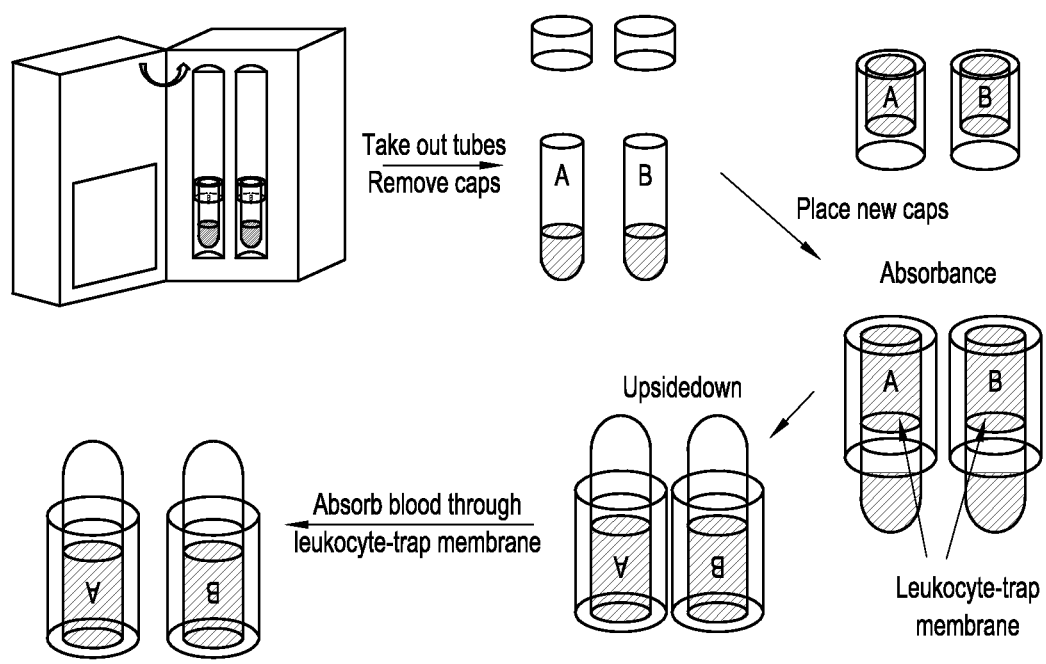
FIG. 3 shows a schematic process for isolating leukocytes from whole blood samples in accordance with some embodiments.
Figure 4:
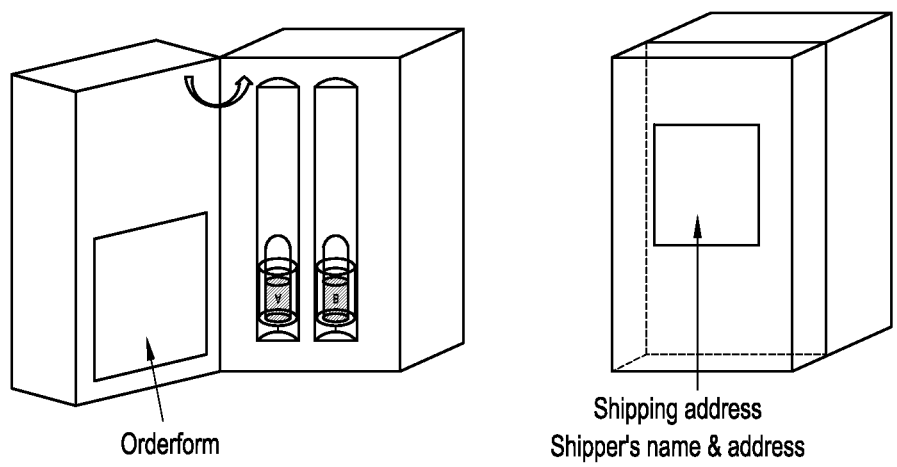
FIG. 4 shows storage and shipment of leukocytes isolated from the whole blood samples in accordance with some embodiments.

Next, as shown in FIG. 3, the stimulated blood samples are removed from the incubator. The cap of the tube is removed and replaced with a cap containing a leukocyte membrane and adsorbing material. The leukocyte membrane is closer to the blood in the tube when the cap is engaged with the tube. Next, after incubation, the tube is inverted thereby causing the blood to contact the leukocyte membrane. Gravity (or other force, depending on the embodiment, e.g., vacuum pressure) assists the filtration of the blood sample. The leukocytes are captured on the membrane and the moisture adsorbing material captures the material that passes through the leukocyte membrane (e.g., plasma, red blood cells, etc.). Next, the two sample tubes are placed back in the incubator in the desired conditions (e.g., −80 degrees C. for storage). As shown in FIG. 4, the incubator is then used to store or ship the samples.

Figure 5:
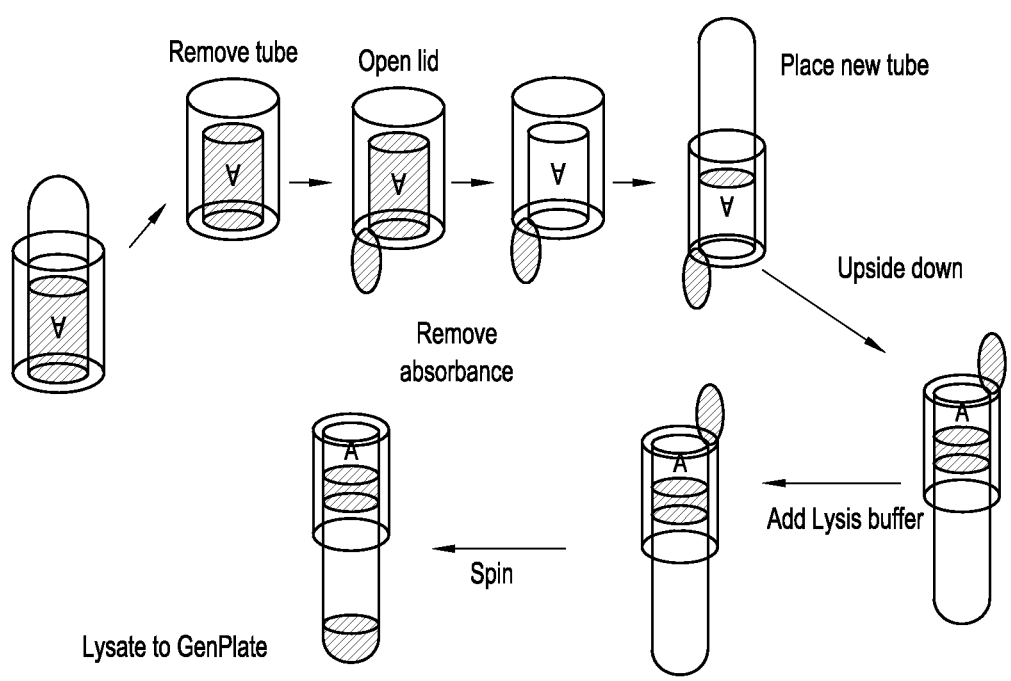
FIG. 5 is a schematic flow chart showing steps for preparing an mRNA assay in accordance with some embodiments.

As shown in FIG. 5, the sample tubes can undergo further steps to prepare an mRNA assay. The cap containing the leukocyte filter membrane and moisture adsorbing material is removed from the tube. The moisture adsorbing material is then removed from a lid on the cap. The leukocyte filter containing the filtered leukocytes is then engaged with a clean sample tube. Next, a lysis buffer is added through the lid in the cap to treat the leukocytes. The tubes are then spun or centrifuged to collect the lysate at the bottom of the tube and transferred to a GENEPLATE, or other collection vessel (s). The amount of the target RNA in the lysate can then be determined by PCR and other methods known in the art.

Example 2—Blood Collection Tube Manufacturing and Testing

Often, blood collection tubes are made of glass, which due to manufacturing defects, exposure to fluctuations in temperature, or mishandling, can break. Given that blood samples are often collected in order to assess the health status of a patient, the blood sample may contain pathogens, chemicals, or other substances that present a danger to the individual(s) collecting and/or analyzing the blood samples. As such, in several embodiments there is provided a non-glass blood collection tube that reduces the risk of tube breakage and unintended exposure of personnel to patient blood samples. Non-glass blood collection tubes, such as those disclosed herein, are advantageous in comparison to traditional glass tubes, as collected blood samples can be stored frozen below −70° C. (e.g., for example after a stimulation protocol), but with a reduced risk of breakage during the thawing process which precedes final analysis. In several embodiments, non-glass tubes comprise polypropylene. In other embodiments, polystyrene tubes are employed. In still additional embodiments, other polymer or plastic tubes that are sufficiently durable to withstand the generation (and maintenance) of negative pressure within the tube and one or more freeze-thaw cycles are used.

Many blood draw tubes operate by having a negative internal pressure (relative to the external environment) that causes blood to flow from a patient (or a separate blood collection device) into the collection tube. This not only allows the blood to be drawn with limited discomfort to the patient, it also prevents back-flow of blood into the patient's venous system.

Figure 7:
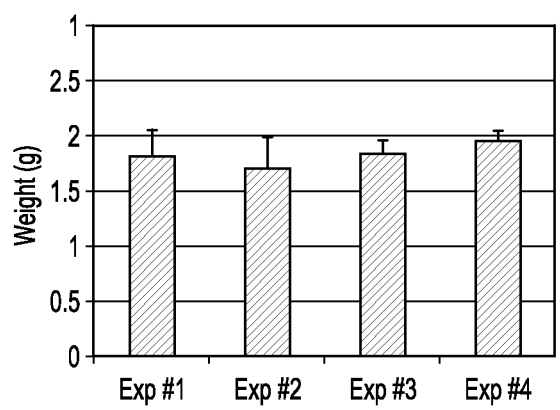
FIG. 7 depicts the reproducibility of manufacturing negative pressure tubes by showing that the weight of water drawn into the tube is not significantly different from tube to tube.

In order to determine the reproducibility of manufacturing non-glass (e.g., plastic tubes having negative internal pressure, plastic tubes with self-sealing puncturable caps were manually made to have negative internal pressure. 3 tubes were made in each of 4 experiments (total of twelve tubes). A 21 gauge needle, with one end submerged in water, was used to puncture the cap, thereby allowing the negative pressure to draw water into the tube. The weight of each set of tubes was then weighed. As shown in FIG. 7, there is no significant difference in the mean weight of the tubes across the experiments, thereby demonstrating that manufacturing of such collection tubes is reproducible.

Figure 8:
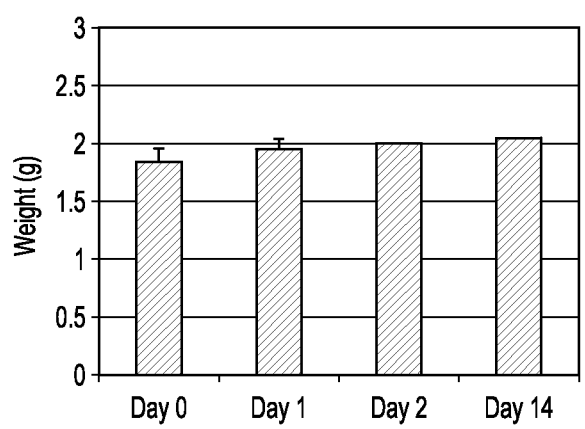
FIG. 8 depicts the stability of manufactured negative pressure tubes after storage by showing that the weight of water drawn into the tube is not significantly different after 14 days of storage after manufacturing.

In addition to reproducibility with respect to sample collection, it is important that a tube has a sufficient shelf life with respect to the maintenance of the negative pressure within the tube and the durability of the tube itself. As such, additional tubes were prepared as described above. They were then stored at room temperature for between 0 and 14 days. As described above, a 21 gauge needle was used to collect water, and the tubes were weighed. FIG. 8 depicts the weights, which show that the negative pressure within the tubes was not different when the tubes were stored for 14 days as compared to storage for 2 days, or compared to immediate use after manufacture.

Example 3—Comparison of Manufactured Blood Collection Tubes and Multi-Well Strips After confirming the reproducibility of manufacturing non-glass blood collection tubes, the following experiments were performed to assess whether such collection tubes perform sufficiently well as more traditional ex vivo blood stimulation methods (e.g., placement of small volumes of blood in wells and individually adding stimulating agents.

Figure 9:
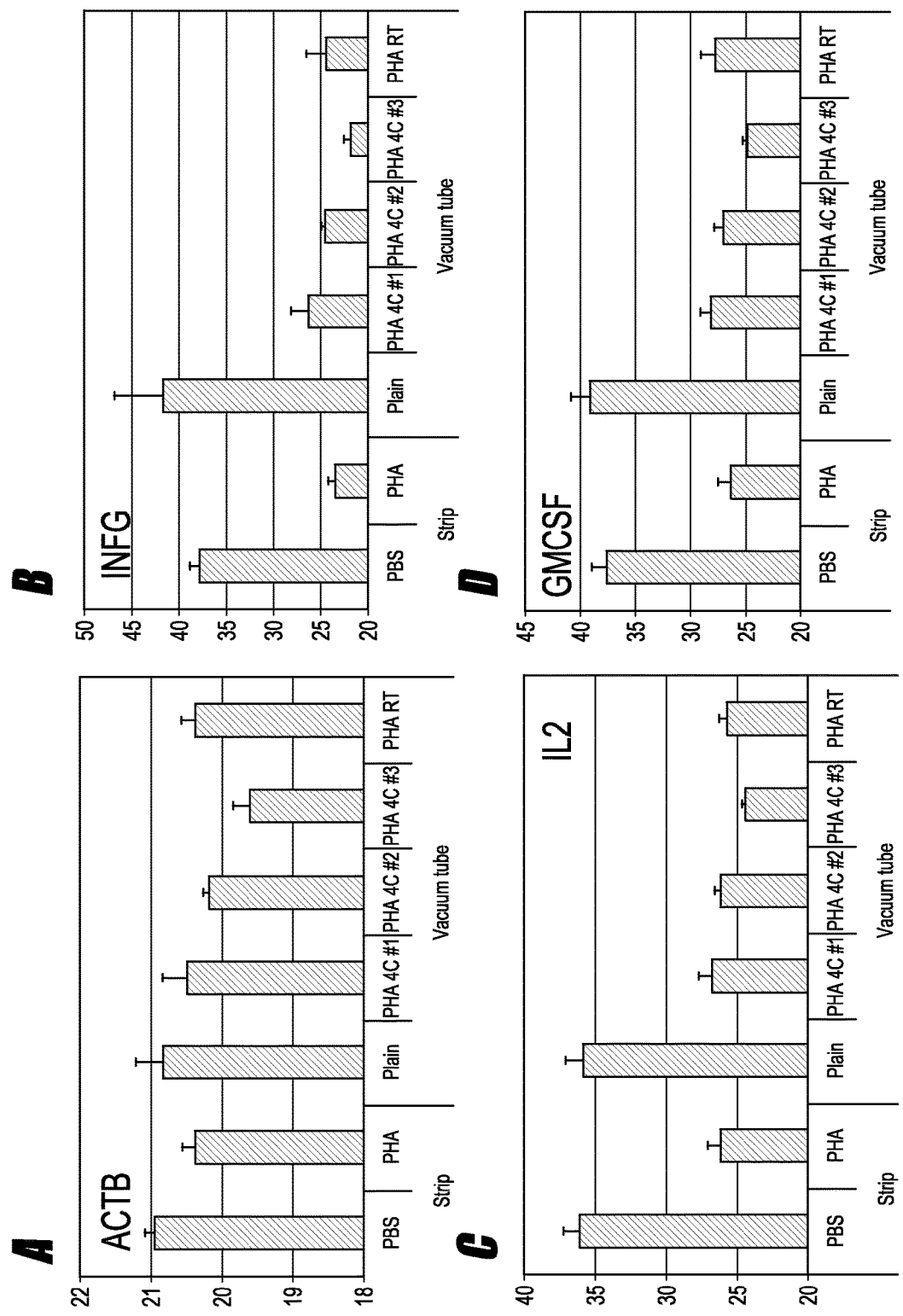
FIGS. 9A-9D shows the comparable results of stimulation experiments performed in manufactured negative pressure tubes as compared to established multi-well strip methods.

Blood collection tubes were manufactured as described above. Three tubes were stored at 4° C. (tubes PHA 4C #1, #2, and #3 in FIG. 9) or room temperature (PHA RT in FIG. 9) for 20 days. Blood was then drawn into 6 tubes: a control heparin tube, a plain heparin tube, and 4 PHA-containing tubes. The blood from the control heparin tube was stimulated (by PBS or PHA) in micro-plate tube strips (3 wells each, 60 µL blood/well). The remaining 5 tubes were incubated at 37° C. for 4 hours. Various mRNA were quantified by using SYBR green real time PCR as described previously (Mitsuhashi M et al. Clin. Chem. 52:634-642, 2006).

Briefly, 96-well filterplates were assembled with leukocyte reduction membranes (Leukosorb; Pall) and placed over oligo(dT)-immobilized collection plates. 150 µL of 5 mmol/L Tris (pH 7.4) was applied to wet the filter membranes. After centrifugation at 120 g for 1 min at 4° C. to remove the Tris solution from the membranes, 50 µL of the stimulated whole blood samples was applied to each well and immediately centrifuged at 120 g for 2 min at 4° C. The wells were then washed once with 300 µL of phosphate-buffered saline. After centrifugation at 2000 g for 5 min at 4° C. to remove the saline solution, 60 µL of stock lysis buffer [5 g/L N-lauroylsarcosine, 4× standard saline citrate, 10 mmol/L Tris-HCl (pH 7.4), 1 mmol/L EDTA, 1 mL/L IGEPAL CA-630 (substitute of NP-40), 1.79 mol/L guanidine thiocyanate (all from Sigma)], supplemented with 10 mL/L 2-mercaptoethanol (Bio-Rad), 0.5 g/L proteinase K (Pierce), 0.1 g/L salmon sperm DNA (5 Prime Eppendorf/ Brinkman), 0.1 g/L $Escherichia$ $coli$ tRNA (Sigma), 5 nmol/L each of the specific reverse primers, and $10^{10}$ molecules/L of synthetic RNA34 (as external control), was added to each well of the filterplates. The plates were then incubated at 37° C. for 10 min, placed over oligo(dT)-immobilized collection microplates (GenePlate; RNAture), and centrifuged at 2000 g for 5 min at 4° C. After overnight storage at 4° C., the microplates were washed 3 times with 100 µL of plain lysis buffer and then 3 times with 150 µL of wash buffer [0.5 mol/L NaCl, 10 mmol/L Tris (pH 7.4) 1 mmol/L EDTA] at 4° C.

cDNA was synthesized directly in each well by addition of 30 µL of buffer containing 1× reverse transcription buffer [50 mM KCl, 10 mM Tris-HCl (pH 8.3), 5.5 mM $MgCl_2$, 1 nL/µL Tween 20], 1.25 mM each deoxynucleoside triphosphate, 4 units of rRNasin, and 80 U of MMLV reverse transcriptase (Promega; without primers) and incubation at 37° C. for 2 h. From each 30-µL reaction, 4 µL of cDNA was transferred directly to 384-well PCR plates, and 5 µL of TaqMan universal master mixture (Applied Biosystems) and 1 µL of 5 µM each of the forward and reverse primers for each mRNA or beta-actin were added. PCR was carried out in a PRISM 7900HT (Applied Biosystems), with 1 cycle of 95° C. for 10 min followed by 45 cycles of 95° C. for 30 s, 55° C. for 30 s, and 60° C. for 1 min. Each gene was amplified in separate wells. The cycle threshold (Ct), i.e., the cycle at which certain amounts of PCR products (based on fluorescence) were generated, was determined with analytical software (SDS; Applied Biosystems). The ΔCt were determined by subtracting each Ct of PHA-treated sample from each Ct of PBS-treated control sample, and the fold increase was calculated by 2^-ΔCt.

As shown in FIGS. 9A-9D, the blood collection tubes show comparable results for control reactions (e.g., compare PBS Strip versus Plain Vacuum Tube). Also, no differences are detected between the PHA-containing tubes that were stored at room temperature versus those stored at 4° C. Finally, for all genes tested (beta-actin, interferon gamma, interleukin 2, and GM-CSF), no differences were detected between the PHA stimulation performed in a multi-well strip format and those performed within the PHA-containing blood collection tubes. These results demonstrate that stimulation of the blood within the blood collection tube is equally as reliable and reproducible as performing the stimulation in a multi-well strip format.

Figure 10:
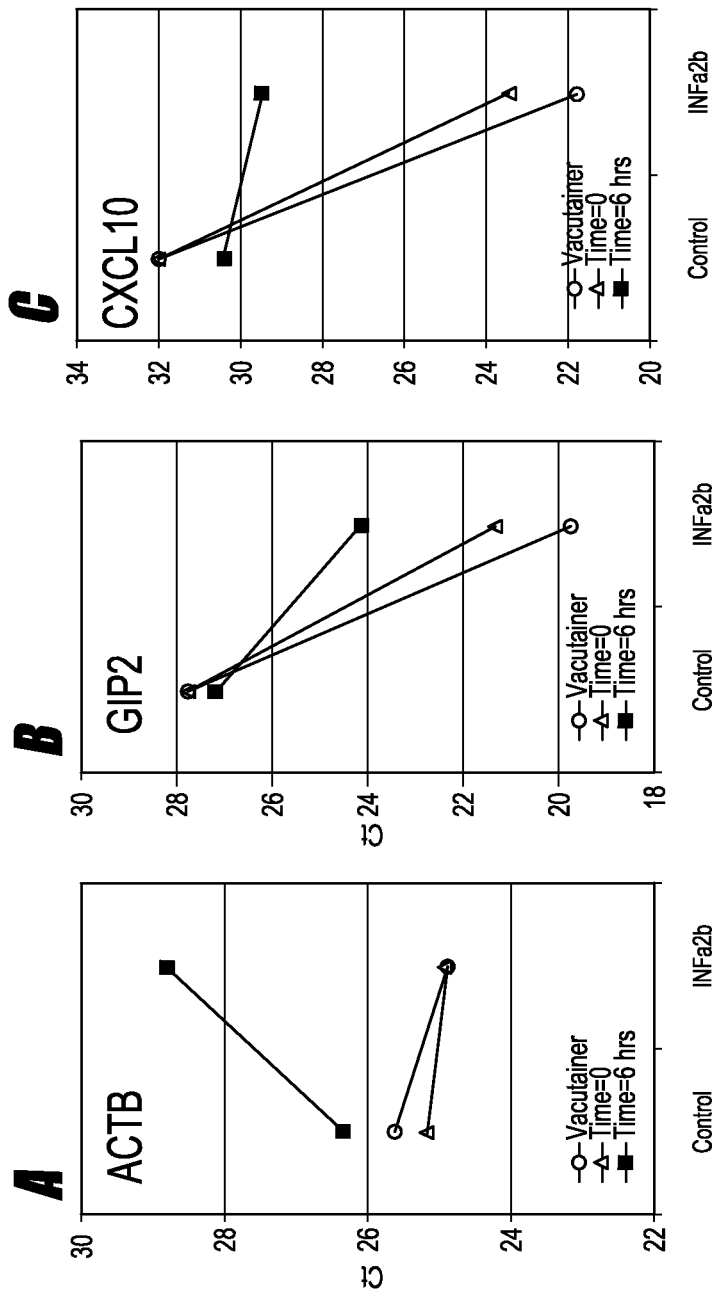
FIGS. 10A-10C show the additional comparable results between gene induction experiments in manufactured negative pressure tubes and established multi-well strip methods.

Additional experiments were performed to determine the effect of delay between the collection of a blood sample and stimulation of the sample. Blood was drawn into 4 heparin containing vacuum tubes manufactured as described above (3 plain tubes and 1 tube with interferon alpha 2b, IFNa2b). Immediately after the blood drawn, one plain tube and the IFNa2b tube were placed in a 37° C. incubator for 2 hour. An additional plain tube was immediately aliquoted into multi-well strip tubes and stimulated with PBS or IFNa2b (3 wells each, 60 µL blood/well) for 2 hours at 37° C. After incubation, each tube was stored −80° C. The final plain tube was stored at 4° C. for 6 hours, and then aliquoted to multi-well strips for stimulation with IFNa2b. As shown in FIGS. 10A-10C, the performance of IFNa2b tube (open triangles)

was identical to that of conventional IFNa2b stimulation in strip wells (open circle). In contrast, blood that was initially stored at 4° C. for 6 hours before ex vivo stimulation showed less induction by IFNa2b for GIP2 and CXCL10 (closed squares). In fact, there may have been degradation of the mRNA during that incubation, as the levels of beta-actin were reduced (FIG. 10A).

Example 4—Stability of Post-Stimulation Blood Samples

In order to evaluate the stability of samples after stimulation, blood was stimulated with DNR (10 µM in final concentration), AraC (100 µM in final concentration), or PBS in strip wells for 4 hours at 37° C., and then stored at 4° C. for 0-3 days. After the 4° C. incubation, the samples were stored in a −80° C. freezer until analysis. These experimental conditions are designed to represent the possible conditions a sample would be exposed to during transport in the portable incubation devices described herein. Three mRNAs (ACTB, p21, and PUMA) were quantified as described above.

Figure 11:
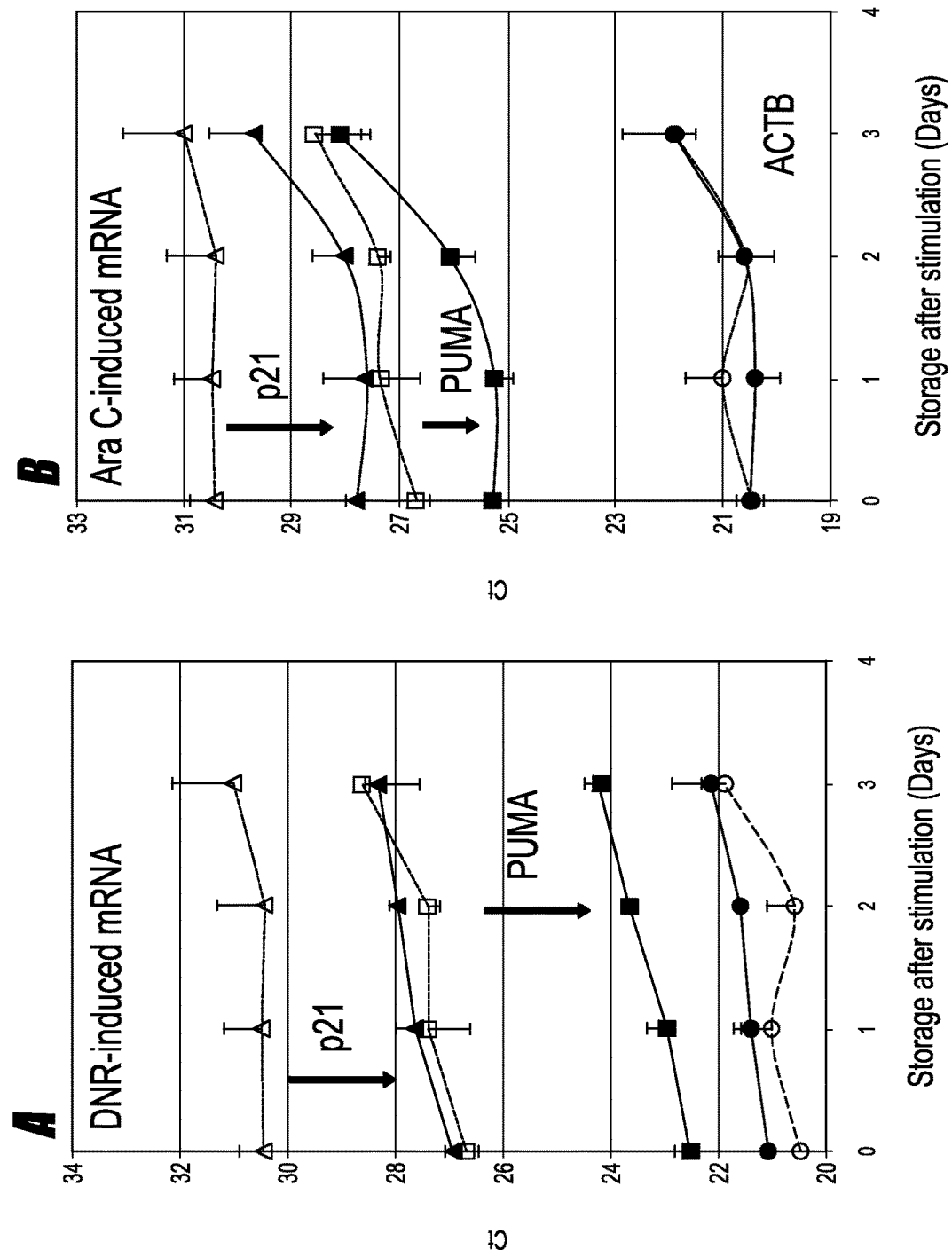
FIGS. 11A-11B depict data related to the stability of blood samples over time and after stimulation.

As shown in FIGS. 11A-11B, beta actin was not induced by either agent (open symbols are PBS controls and closed symbols are DNR or AraC stimulation) and the levels of beta actin mRNA were relatively stable over the 3 days. FIG. 11A shows that DNR induced significant induction in p21 (arrow between open and closed triangles). Similar results were obtained with AraC stimulation (FIG. 11B). Likewise, both agents induced PUMA expression. After 1 day of storage post-stimulation, expression levels of p21 and PUMA were similar to those at Day 0. However, after 3 days of post-stimulation storage, levels of both p21 and PUMA appear to have decreased (higher Ct values) for both stimulating agents. There is also an apparent increase at Day 1 post-stimulation. As such, these results indicate that in some embodiments, 2 days of storage post-stimulation could be possible. In several embodiments, however, post-stimulated blood can be stored at 4° C. for 1 day.

The time course of induction was also evaluated for two different incubation temperatures. This is to evaluate the time for which a sample can be exposed to an incubation temperature and still provide reliable and consistent gene expression data. Blood was stimulated with PHA, IFNa2b, or PBS (in triplicate) in strip wells at either 37° C. or 42° C. for 0-9 hours, then stored frozen at −80° C. These temperatures represent the operative range of small portable heaters that are used in some embodiments of the portable incubation and storage devices disclosed herein. ACTB, IL2, and CXCL9 mRNA were quantified.

Figure 12:
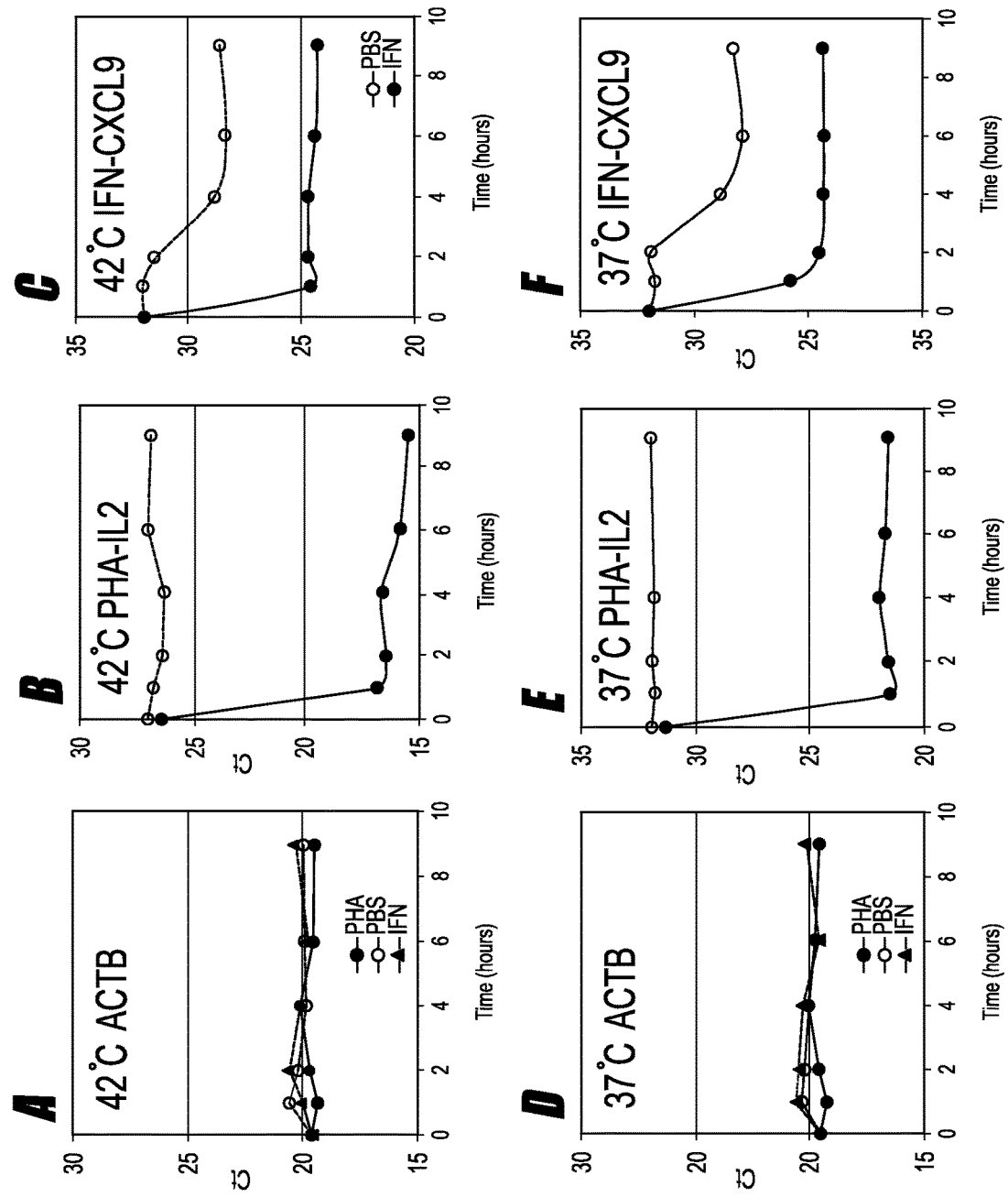
FIGS. 12A-12F depict data related to the levels of gene induction as a result of stimulation and incubation at different temperatures.

As shown in FIGS. 12A and 12D, incubation of blood samples at either 40° C. or 37° C. did not change the expression of beta-actin, regardless of the stimulating agent. FIGS. 12B and 12E demonstrate that the induction of IL-2 mRNA by incubation with PHA is similar whether performed at 42° C. or at 37° C. Moreover, expression levels are similar when performed at any point between 1 hour and 9 hours of stimulation. Similarly, in FIGS. 12C and 12F, CXCL-9 was induced to a similar extent by interferon regardless of the incubation temperature or duration of incubation. Thus, in several embodiments, a great degree of flexibility exists in terms of the stimulation conditions used. This allows the shipment of samples from a greater variety of locations, as greater distances could be covered in a 9 hour incubation period versus a 1 hour incubation. Also, in several embodiments, this flexibility is advantageous in selecting heating elements, as the options for the type of heating device used are greater given the wider range of incubating times.

Figure 13:
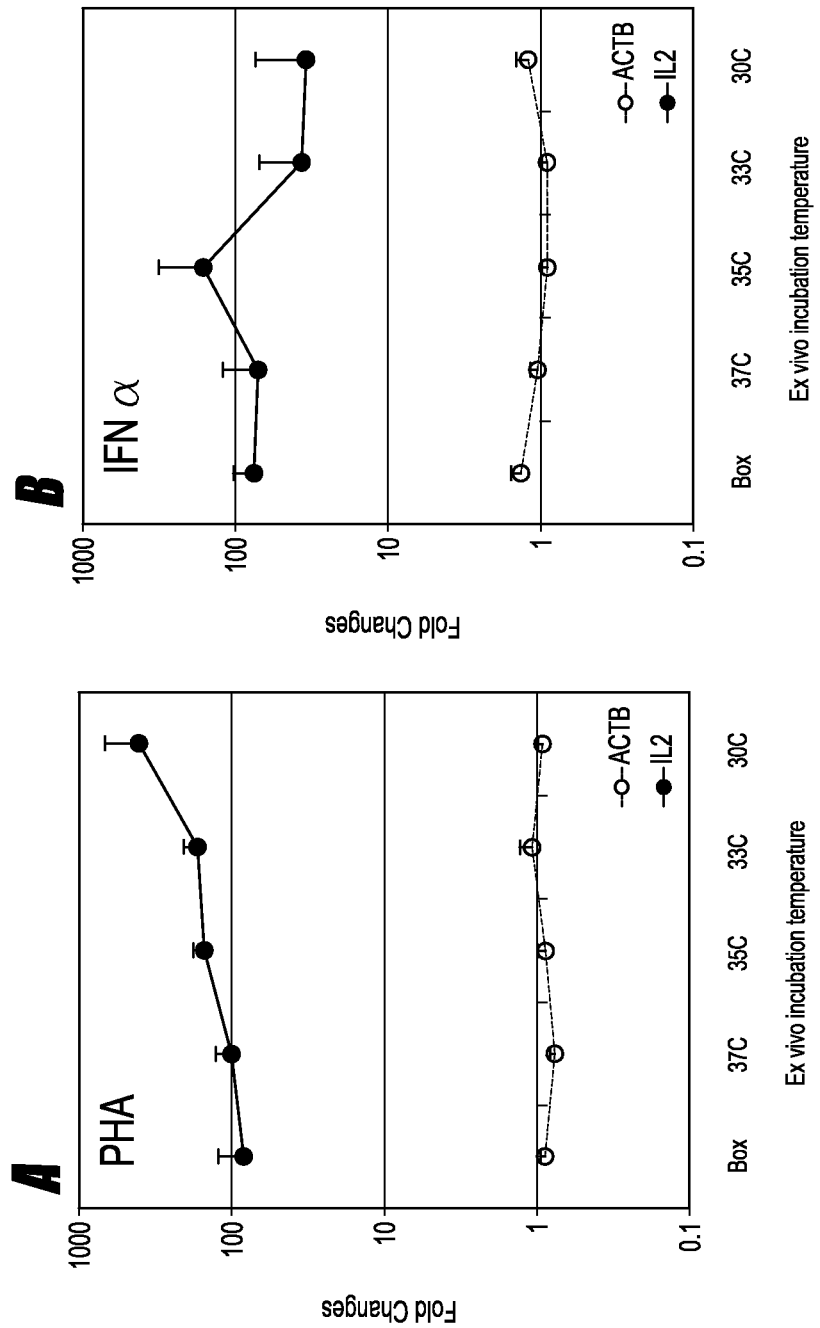
FIGS. 13A-13B depict data related to the levels of gene induction as a result of incubation in a portable device as disclosed herein as compared to temperature controlled incubators.

FIGS. 13A and 13B depict a comparison of the level of induction of IL2 or CXCL9 when stimulated by PHA or IFN alpha and then incubated in the portable device disclosed herein or in controlled incubators (at a variety of temperatures). As shown, both IL2 and CXCL9 induction were not significantly different when the incubation occurred using the portable device as compared to controlled incubators. This again represents the degree of flexibility in temperatures and times that can be used (as disclosed above) to perform ex vivo stimulation of blood samples.

Figure 14:
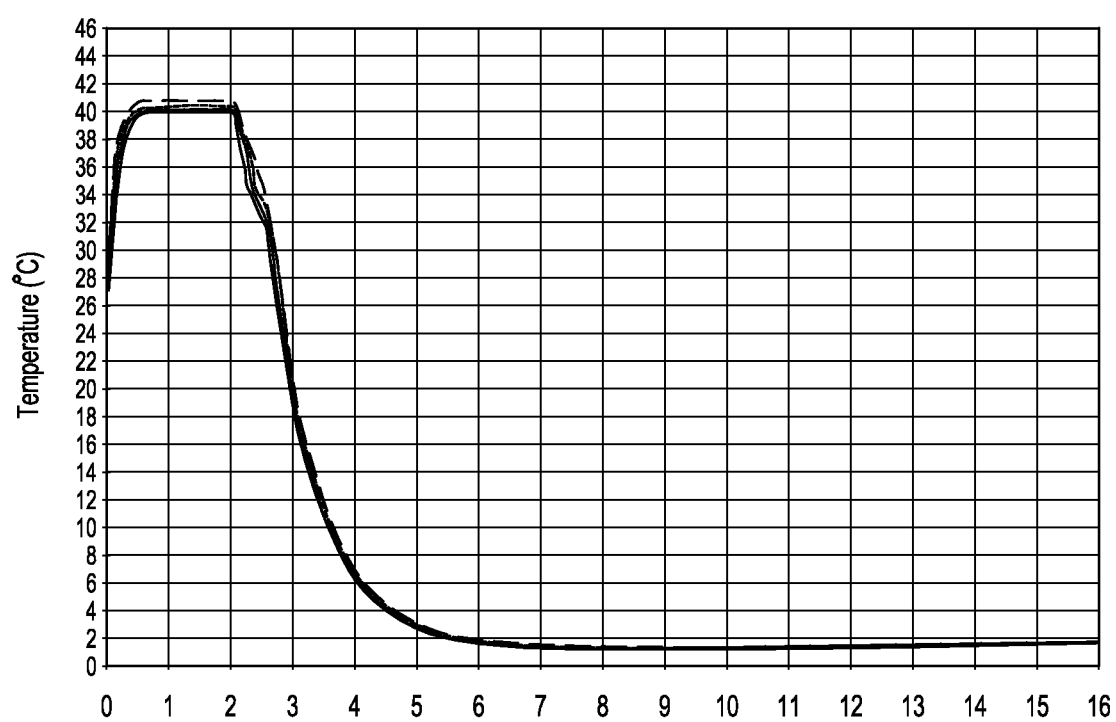
FIG. 14 depicts temperature curves recorded from 6 individual tubes incubated in the portable device disclosed herein.

FIG. 14 depicts temperature profiles recorded from six temperature loggers, each loaded in one of six blood collection tubes and placed in a copper box attached to battery-operated heat sources. The copper box was placed within the portable device as described above along with two blue ice packs. These data demonstrate that, even in the presence of the blue ice, the temperature within the copper box was maintained at 40° C. for two hours as a result of the heat sources. Once the heat sources shut off, the temperature dropped to 2° C. and was maintained until 16 hours. There was no discernable tube-to-tube variation, which indicates that positioning of the sample tubes within the copper box does not impact the incubation temperatures.

It will be appreciated by those skilled in the art that various omissions, additions and modifications may be made to the devices and methods described above without departing from the scope of the invention, and all such modifications and changes are intended to fall within the scope of the invention, as defined by the appended claims.

What is claimed is:

1. A system for the ex vivo stimulation of blood, the system comprising:
   an insulated shell having an internal cavity;
   a box disposed within said internal cavity of said insulated shell,
      wherein said box is dimensioned to contain a plurality of blood collection tubes;
   a heating device contained within said box,
      wherein said heating device is adapted to maintain a temperature within the box at a first temperature in a range between 25° C. and 40° C. for a first period of time,
      wherein said first period of time is at least one hour after activation of the heating device,
      wherein said heating device is adapted to be inactivated after said first period of time has elapsed, and
      wherein a temperature fluctuation around said maintained temperature is within ±2.5° C.;
   a cooling source disposed within said internal cavity and outside of said box,
      wherein said cooling source is adapted to be active with said heating device during said first period of time, and
      wherein said cooling source is adapted to be active after said first period of time to maintain a temperature of the internal cavity at a second temperature of 4° C.±5° C. for a second period of time of at least 4 hours after said first period of time has elapsed; and
   a battery source electrically coupled to the heating device, the battery source configured to power the heating device to allow the heating device to heat the inside of the box to the first temperature for said first period of time with the cooling device having a temperature in a range between 0° C. and 4° C. during said first period of time.

2. The system of claim 1, wherein said first temperature phase comprises a maintained temperature of 37° C.±2.5° C. and wherein said second temperature phase comprises a maintained temperature of 4° C.±5° C.

3. The system of claim 1, further comprising a plurality of blood collection tubes, said blood collection tubes comprising an anti-coagulant and a stimulating agent.

4. The system of claim 3, wherein the stimulating agent is selected from the group consisting of a chemotherapeutic drug, immunomodulatory agent, vaccine, adjuvant, recombinant protein, monoclonal antibody, lectin, derivatives from infectious agents, allergens, and combinations thereof.

5. The system of claim 3, further comprising a second plurality of blood collection tubes comprising the anticoagulant and a corresponding control solvent of said stimulating agent.

6. The system of claim 3, wherein said blood collection tubes comprise
a non-glass tube;
the anticoagulant;
the leukocyte stimulating agent; and
a puncturable self-sealing cap that seals the collection tube,
wherein a pressure within the collection tube is negative as compared to the pressure outside of the collection tube.

7. The system of claim 6, wherein the blood collection tubes further comprise a visible marker of that is activated by negative pressure.

8. The system of claim 1, further comprising a temperature recording device, wherein said device serially records the temperature within said cavity for later retrieval.

9. The system of claim 1, wherein said heating device is battery operated, wherein said battery comprises one or more primary batteries or one or more secondary batteries.

10. The system of claim 9, wherein said heating device generates heat through a chemical reaction.

11. The system of claim 9, wherein said temperature recording device is battery operated, wherein said battery comprises one or more primary batteries or one or more secondary batteries.

12. The system of claim 1, wherein said cooling source comprises a re-usable coolant.

13. The system of claim 1, wherein said heating source is regulated by a timer, wherein said timer is programmed to inactivate the heating source after said first period of time has elapsed.

14. The system of claim 1, wherein said box comprises a copper box.

15. A method for the ex vivo stimulation of a blood sample, the method comprising:
collecting a first blood sample from a subject into a blood collection tube comprising a non-glass tube, one or more anticoagulants, and one or more leukocyte stimulating agents;
placing the blood collection tube into a system according to claim 1 such that the blood collection tube is disposed in said box of said system;
activating said heating device and powering said heating device with said battery source for said first period of time to maintain a temperature within said box in a range between 25° C. and 40° C. for said first period of time, thereby stimulating the blood sample ex vivo;
placing said cooling source within said internal cavity;
maintaining said internal cavity at said second temperature with said cooling source for said first period of time,
inactivating said heating device after said first period of time has elapsed to thereby allowing said box to cool, thereby achieving said second temperature within said box; and
maintaining the second temperature within said box for said second period of time which is at least 4 hours after said first period of time has elapsed.

16. The method of claim 15, further comprising:
after performing said placing the blood collection tube into said system, transporting said system from a first location to a second location that is spaced apart from the first location.

17. The method of claim 16, wherein the transporting is performed during at least a portion of said first period of time.

18. A system for ex vivo stimulation of blood during transport of the blood, the system comprising:
an insulated shell;
a box sized to fit within the insulated shell;
a heat source attached to the box, wherein said heat source is adapted to maintain a temperature within the box at a first temperature in a range between 25° C. and 40° C. for a first period of time;
a re-usable ice pack disposed within the insulated shell and outside of the box, wherein said re-usable ice pack is active with said heat source during said first period of time, wherein the re-usable ice pack is adapted to maintain a temperature within the insulated shell at a second temperature of 4° C.±5° C. for a second period of time of between 24 to 72 hours, wherein the second period of time period includes the first period of time; and a battery source electrically coupled to the heating device, the battery source configured to power the heating device to allow the heating device to heat the inside of the box to maintain the inside of the box at the first temperature for said first period of time with the re-usable ice pack having a temperature in a range between 0° C. and 4° C. during said first period of time.

19. The system of claim 18, wherein said box comprises a copper box.

* * * * *